(12) United States Patent
Shalom et al.

(10) Patent No.: US 6,464,646 B1
(45) Date of Patent: Oct. 15, 2002

(54) INSTRUMENT AND METHOD FOR LOCATING AND MARKING A HOT SPOT IN A PERSON'S BODY TISSUE

(75) Inventors: Moshe Shalom, Herzlia; Shai Ghilai, Tel Aviv; Alex Weizer, Kfar Saba, all of (IL)

(73) Assignee: Veino-Med Ltd., Netanya (IL)

( * ) Notice: Subject to any disclaimer, the term of this patent is extended or adjusted under 35 U.S.C. 154(b) by 0 days.

(21) Appl. No.: 09/646,960

(22) PCT Filed: Mar. 23, 1999

(86) PCT No.: PCT/IL99/00162
§ 371 (c)(1),
(2), (4) Date: Feb. 1, 2001

(87) PCT Pub. No.: WO99/48420
PCT Pub. Date: Sep. 30, 1999

(30) Foreign Application Priority Data

Mar. 23, 1998 (IL) .................................................. 123787

(51) Int. Cl.⁷ .................................................. A61B 5/00
(52) U.S. Cl. ........................................ 600/549; 600/481
(58) Field of Search .............................. 600/473, 474, 600/479, 481, 549; 374/112, 120, 121, 137, 186; 356/51; 250/330, 334

(56) References Cited

U.S. PATENT DOCUMENTS

| | | | |
|---|---|---|---|
| 3,782,365 A | * 1/1974 | Pinna | 600/481 |
| 3,973,124 A | 8/1976 | Astheimer | 250/334 |
| 3,998,210 A | * 12/1976 | Nosari | 600/549 |
| 4,173,970 A | 11/1979 | Momin | 600/549 |
| 4,445,516 A | * 5/1984 | Wollnik et al. | 600/549 |
| 4,817,622 A | 4/1989 | Pennypacker et al. | 600/473 |
| 5,519,208 A | 5/1996 | Esparza et al. | 250/226 |
| 5,608,210 A | 3/1997 | Esparza et al. | 250/226 |
| 5,678,555 A | 10/1997 | O'Connell | 600/479 |
| 6,056,692 A | * 5/2000 | Schwartz | 600/443 |

FOREIGN PATENT DOCUMENTS

DE   30 20 359 A1   12/1981

\* cited by examiner

*Primary Examiner*—Kevin Shaver
*Assistant Examiner*—Charles Marmor, II
(74) *Attorney, Agent, or Firm*—Browdy and Neimark, P.L.L.C.

(57) ABSTRACT

A portable passive instrument (10) and a method for locating and marking at least one area of a person's body tissue, such as a vein, having a local variation in temperature compared with surrounding body tissue. The temperature along at least a line of skin within a region of the body tissue is scanned so as to obtain discrete signals representative of respective temperatures of discrete portions along an unstimulated portion of the at least a line of skin. The resulting signals are analyzed so as to derive a temperature profile in order to determine the at least one area having local temperature variation, which is then marked either optically or by means of a pigment.

23 Claims, 8 Drawing Sheets

INSTRUMENT AND METHOD FOR LOCATING AND MARKING A HOT SPOT IN A PERSON'S BODY TISSUE

CROSS REFERENCE TO RELATED APPLICATION

The present application is the national stage under 35 U.S.C. 371 of PCT/IL99/00162, filed Mar. 23, 1999.

FIELD OF THE INVENTION

The present invention relates to location of a "hot spot" in a patient's body tissue, particularly a vein.

BACKGROUND OF THE INVENTION

The need for accurate location of a patient's vein for the purpose of medical procedures is well known. The task can be relatively simple when a needle must be inserted into a superficial vein but the procedure can be hit and miss in those cases wherein it is necessary to locate veins which are several millimeters beneath the skin surface. Known techniques usually rely on effecting a local increase in blood pressure by application of a tourniquet so as to cause protuberance of the veins but this is not always effective and, in any case, is apt to be unsuitable other than for superficial veins.

U.S. Pat. No. 4,817,622 (Pennypacker et al.) discloses an infrared imager for viewing subcutaneous location of vascular structures based upon the infrared radiation of a patient's limb. A video camera which is sensitive to infrared radiation produces a video image highlighting contrasting portions of the flesh which are infrared absorbing or infrared scattering. This permits location of those veins which would otherwise be hard to find.

U.S. Pat. No. 5,608,210 (Esparza et al.) describes a device for aiding a technician to locate a vein for inserting a hypodermic needle therein, again based on the infrared radiation of an appropriate area of the flesh so as to highlight the location of a subcutaneous vein. The resulting heat contour, which allows the vein to be highlighted, is imaged using an infrared-sensitive video camera and the image is displayed so as to allow the ready location of the vein.

Likewise, U.S. Pat. No. 5,519,208 (also to Esparza et al.) discloses a method and apparatus for gaining intravenous access wherein, again, a source of radiation is required for irradiating an area of the patient. The wavelength of the radiation is such that the radiation is absorbed in areas containing veins and reflected in all other areas whereby an image of the irradiated area permits the irradiated vein to be readily contrasted from the surrounding area.

All of the above-referenced patents have in common the provision of an external source of infrared radiation and the subsequent display of the resulting heat contour, which permits the vein to be highlighted. Such an approach requires not only an external source of infrared radiation but, moreover, expensive infrared imaging and display apparatus.

U.S. Pat. No. 5,678,555 (O'Connell) discloses a non-invasive method for locating blood vessels in a live human body using infrared scanning and imaging techniques to distinguish relative temperature differences between blood carrying vessels and surrounding human tissue. An infrared imaging camera is used to detect the emissions of an object to differentiate the specific elevated surface temperature associated with blood vessels in a human body and surrounding tissue. The veins can then be marked. O'Connell thus obviates the need for an external source of infrared radiation but his temperature profile is displayed qualitatively in the form of an infrared thermal image allowing a hotspot to be seen visually by an operator of the infrared imaging camera.

DE 30 20 359 (Hermann) discloses a procedure for the capture and display of thermographs of biological or technical structures, whereby in addition to the display of the local temperature distribution, the temperatures at each pixel of a thermograph are digitally captured and displayed on a TV monitor. Although digital imaging is employed, no digital processing is suggested and hot spots are displayed qualitatively using color variations to distinguish between different temperatures of the scanned tissue.

It thus emerges that whilst both U.S. Pat. No. 5,678,555 and DE 30 20 359 disclose passive thermal imaging techniques, they both display the resulting temperature profile qualitatively in a visual manner, thus allowing a hot spot to be identified from the thermal image. In practice, a hot spot may relate to a single vein or to multiple veins in close proximity and neither of these references is capable of distinguishing whether the hot spot is indicative of a single vein or of multiple veins. Still less can these references actually distinguish between the veins themselves in the event that a hot spot relates to multiple veins in close mutual proximity and having variable depth distribution. Therefore, whilst they will correctly mark a lone vein, they are liable to miss the most suitable vein when it is one of multiple veins in close mutual proximity. This is a significant drawback particularly bearing in mind that a priori there is no way to distinguish from the thermal image whether a hot spot relates to a single vein or to multiple veins in close mutual proximity.

SUMMARY OF THE INVENTION

It is therefore an object of the present invention to provide an instrument, which locates and marks a vein for the purpose of allowing accurate alignment of a needle therewith or any other medical procedure.

According to a broad aspect of the invention there is provided a portable passive instrument for locating and marking at least one area of a person's body tissue having a local variation in temperature compared with surrounding body tissue, said instrument comprising:

temperature scanning means for scanning along the person's skin within a region of said body tissue so as to obtain signals representative of a temperature profile along an unstimulated portion of the skin, processing means coupled to said temperature scanning means for analyzing said signals so as to derive the temperature profile in order to determine said at least one area having local temperature variation, and marking means for marking said at least one area;

characterized in that:

the temperature scanning means is adapted for scanning along at least a line of skin within the region of said body tissue so as to obtain discrete signals representative of respective temperatures of discrete points along an unstimulated portion of the at least a line of skin, the processing means is further adapted to process the temperature profile by determining first and second derivatives of the temperature profile in order to compensate for a possible influence of multiple veins in close mutual proximity so as to determine a location of each vein within the scanned region of body tissue, and the marking means is adapted to mark at least one vein within the scanned region of body tissue.

The marking means may be a point of light, which is directed on to the skin so as to allow automatic alignment of an injection needle therewith. Alternatively, it can mark the location of the vein with a small spot of ink so as to allow subsequent manual injection.

Preferably the temperature scanning means includes an infrared detector for detecting infrared radiation having a wavelength of between 3–20 µm and includes suitable folding optics for allowing the skin to be scanned.

BRIEF DESCRIPTION OF THE DRAWINGS

In order to understand the invention and to see how the same may be carried out in practice, a preferred embodiment will now be described by way of non-limiting example, with reference to the accompanying drawings, in which.

DETAILED DESCRIPTION OF A PREFERRED EMBODIMENT

Figure 1:
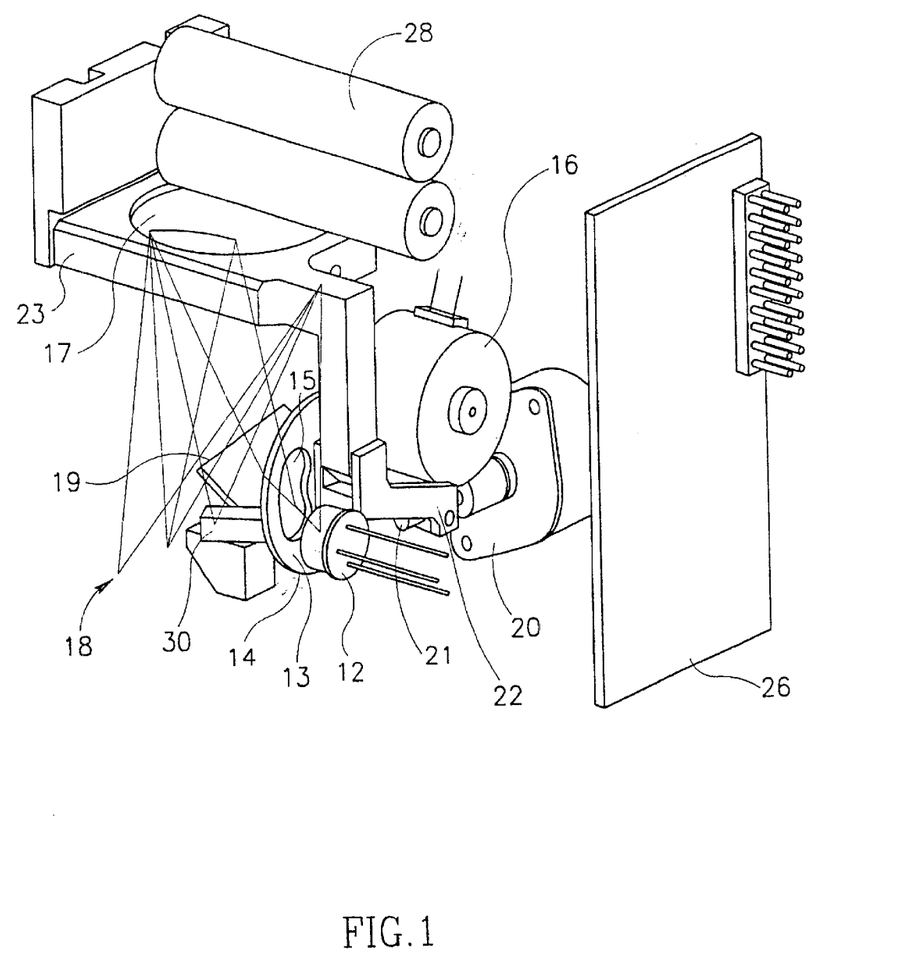
FIG. 1 is a perspective view of an instrument according to the invention.
Figure 2A:
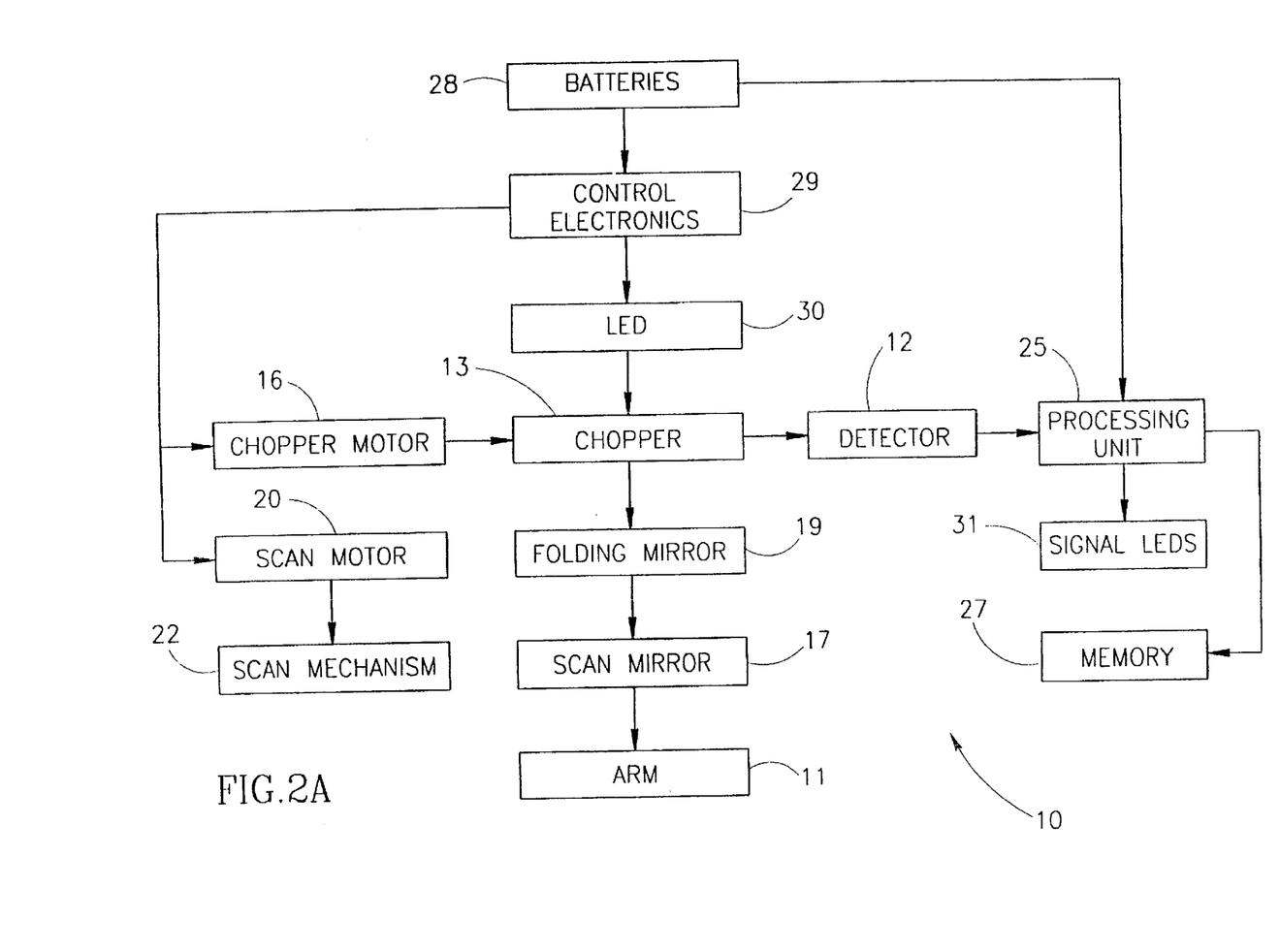
FIG. 2A is a block diagram showing functionally the principal components of the instrument illustrated in FIG. 1.
Figure 2B:
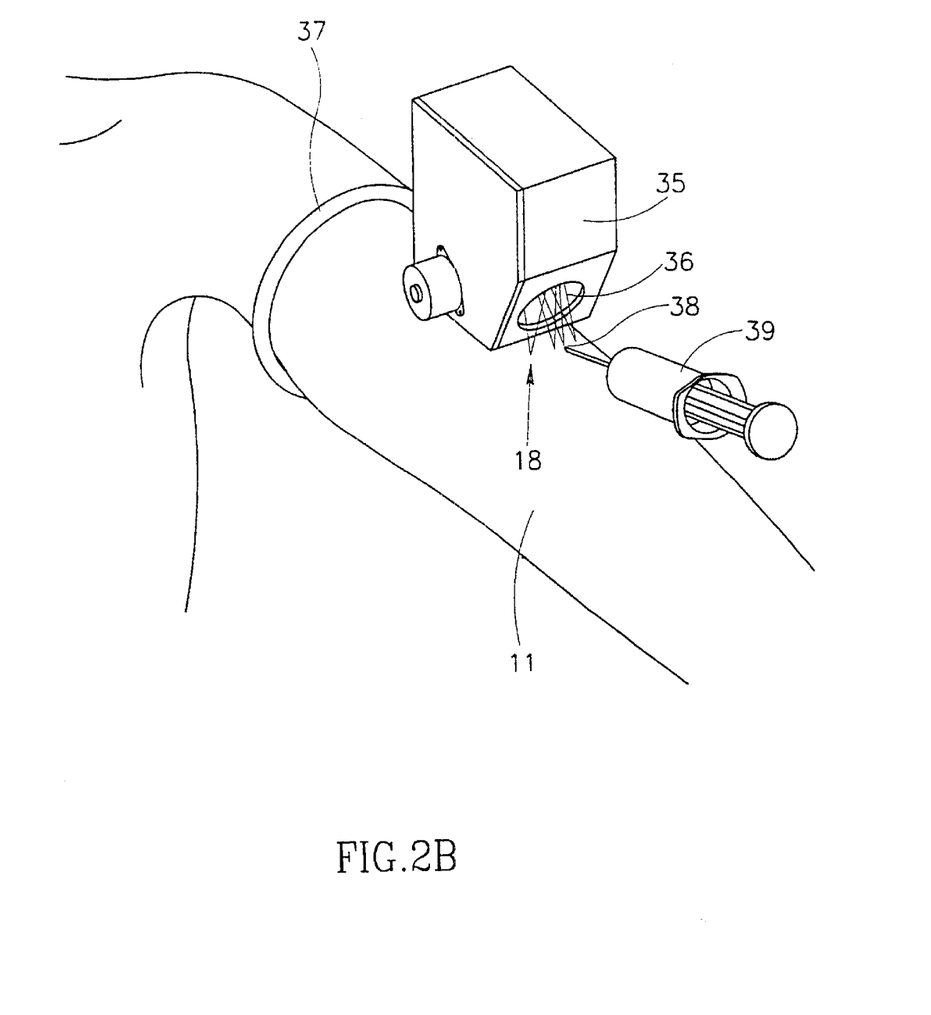
FIG. 2B shows pictorially use of the instrument in situ illustrated in FIG. 1 so as to allow manual injection through a patient's vein.

FIGS. 1, 2A and 2B show pictorially and functionally, respectively, an instrument designated generally as 10 for locating and marking a vein within a patient's arm 11. An infrared detector 12 is adapted thermally to image the arm 11 in the infrared range via a chopper 13. The chopper 13 comprises a rotating disc 14 having a pair of slots 15. A chopper motor 16 rotates the chopper 13 so that the infrared detector 12 thermally images the arm 11 at a rate of approximately 1–10 Hz. The imaging is effected by means of a scan mirror 17 directed towards the arm 11 so as to image a point 18 on the arm 11. The focused image is directed to a folding mirror 19 from which a reflected beam is directed to the infrared detector 12.

In order to image successive points along an area of the patient's arm 11, the scan mirror 17 must be successively moved along a width of the arm 11. To this end, there is provided a scan motor 20, a shaft 21 of which is mechanically coupled via a scan mechanism 22 to a mount 23 in which the scan mirror 17 is mounted. By such means, successive points along the scan area are thermally imaged by the infrared detector 12. An output of the infrared detector 12 is fed to a processing unit 25 mounted on a printed circuit board (PCB) 26 on which there is also mounted a memory 27 in which successive detector signals, each corresponding to a known position of the scan mirror 20, are stored. The processing unit 25 and the associated electronics on the PCB 26 are powered by means of two penlight batteries 28.

Rotation of the chopper motor 16 and the scan motor 20 are controlled via a control electronics 29 also mounted on the PCB 6. A LED 30 (constituting a point light source) is coupled to the control electronics 29 for producing a light beam that can signal at least one hot spot as a local variation in temperature compared with surrounding body tissue. The processing unit 25 collects and stores in the memory 27 successive detector signals each of which is associated with a known position of the scan motor 20. The stored data is processed in order to identify the maximum signal corresponding to the point of highest temperature (constituting a "hotspot") due to blood flow through a vein thereby signaling the location of the vein. Under control of the processing unit 25, the scan motor 20 is now rotated so that the LED 30 is aligned with the same point which is thus marked by the LED light beam or by a suitable pigment.

At least a pair of signal LEDs 31 are coupled to the processing unit 25 for visually indicating a status thereof. Thus, one of the LEDs 31 shows that the instrument 10 is energized, whilst the other is illuminated when a vein has been successfully located. In the event that no vein is successfully identified, a suitable audible or visible warning signal may be provided.

FIG. 2B shows pictorially the instrument 10 mounted within a housing 35 having an aperture 36 for allowing the successive focused scan beams to emerge therefrom onto the patient's arm 11. In use, a tourniquet 37 is applied to an upper portion of the patient's arm 11 near to the biceps so as to cause a local increase in blood pressure which, in turn, increases the sensitivity of the instrument. Also shown in the figure is a point 38 corresponding to the location of a vein as marked by the LED 30 so as to allow accurate alignment with a syringe 39.

Figure 3A:
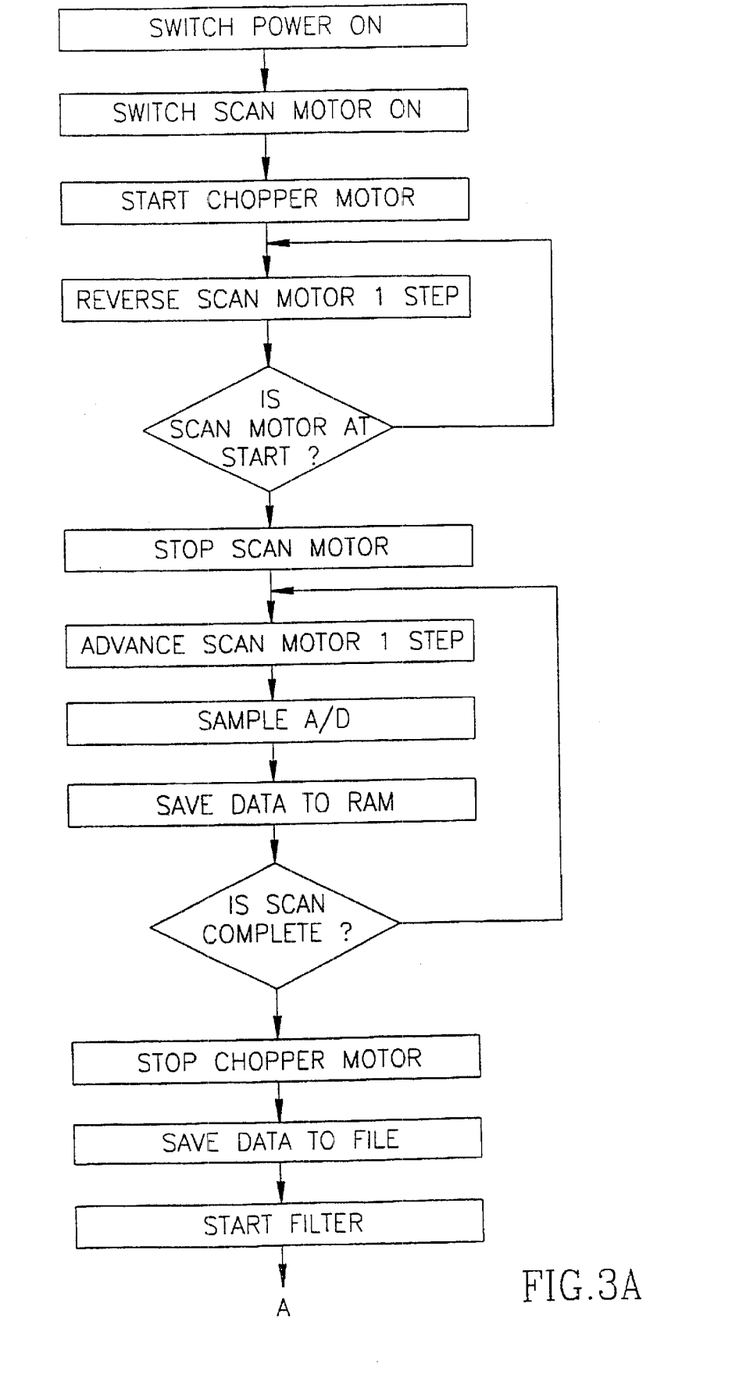
FIGS. 3A and 3B are a flow diagram showing the principal operating steps associated with the instrument illustrated in FIG. 1.
Figure 3B:
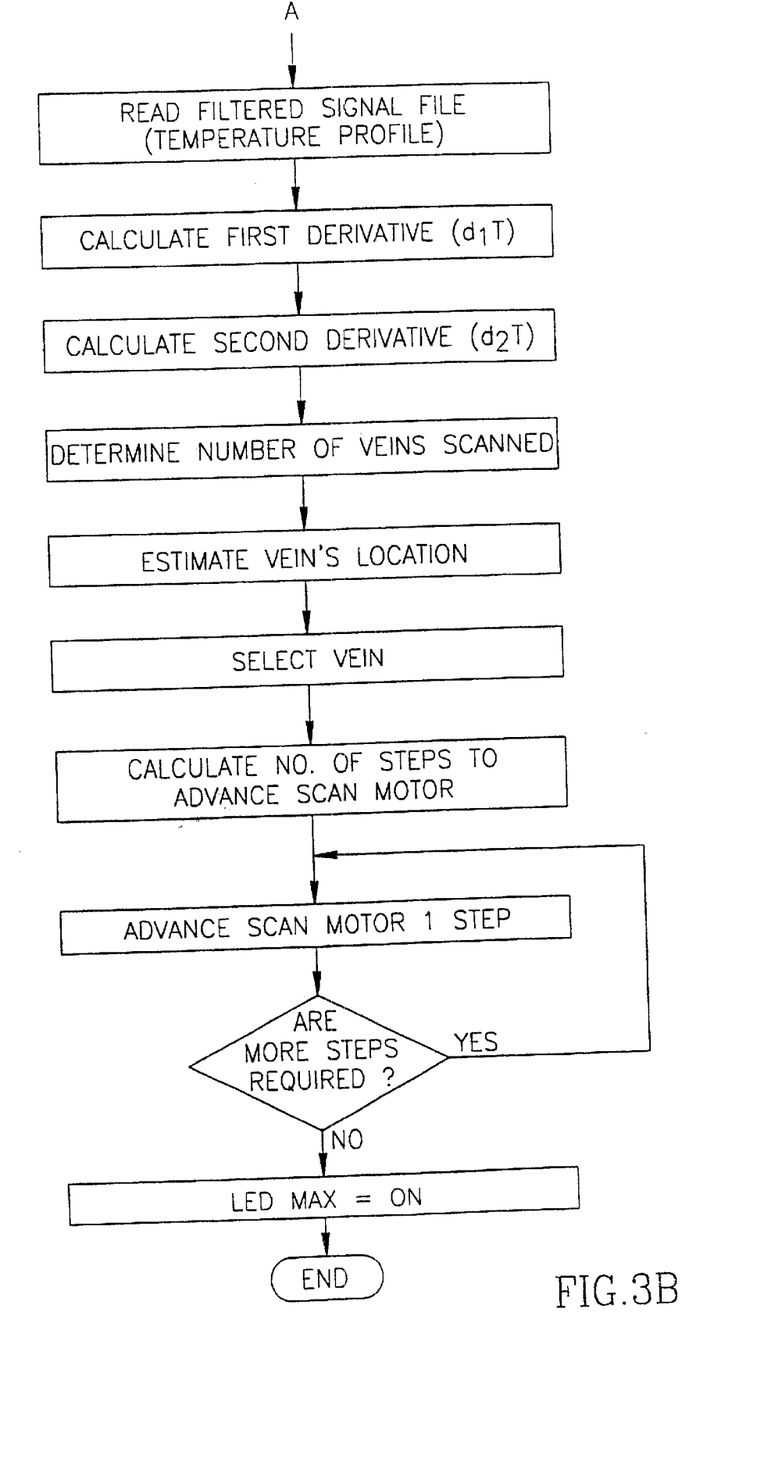

Referring now to FIGS. 3A and 3B, there is shown a flow diagram of the principal operating steps associated with the processing unit 25. On "power on", the scan motor 20 is initialized and the chopper motor 16 is actuated. The processing unit 25 performs two distinct stages of operation: the first stage wherein the scan optics is operative; and a subsequent second stage wherein the scan data stored in the memory 27 is processed. During the first stage, having switched on the scan motor, it is rotated in a reverse direction until the infrared detector 12 is aligned with an initial location corresponding to a known position of the scan motor 20. The scan motor 20 is then stopped and is advanced in a forward direction at discrete steps so as to scan successive discrete points along a line. Each successive scan point is thermally imaged by the infrared detector 12 which produces a signal whose magnitude is substantially proportional to the measured temperature. The measured data is stored in the memory 27 so that during the complete scan cycle successive locations in the memory each correspond to successive scan points which, in turn, may be correlated to a known position of the scan motor 20.

At the end of the scan cycle the scan motor is stopped, the data in the memory 27 is stored in a file so as to be processed under control of the processing unit 25 in order to determine the maximum signal. In the event that only a single vein is scanned, the maximum signal affords an unambiguous indication of the vein's location. However, in the more general case, there may be several veins in close proximity to one another and having variable depth distribution. In order to accommodate this situation and still provide a reliable indication of a suitable vein's location, the temperature profile must be further processed as explained in greater detail below with reference to FIGS. 5 to 7 of the drawings.

Thus, as described below, the filtered signal corresponding to the temperature profile is read from the data file and the first and second time derivatives calculated (i.e. dT/dt and $d^2T/dt^2$, respectively). This permits the number of veins which were scanned to be determined even in the case that the veins are located very close to each other at different transverse locations along the scan area. Thereafter, the respective location of each vein is estimated and that vein giving rise to the maximum hot spot is selected.

The scan motor 20 is then moved under control of the control electronics 29 to that position which correlates with the scan point of maximum amplitude whereupon the LED 30 is illuminated or a pigment is applied to the skin so as to mark the point of maximum temperature corresponding to the location of a vein.

In the event that more than one vein is scanned by the instrument 10, then that vein which gives rise to maximum local heating is the one which will be detected and whose location will be marked by the LED 30. In practice, this will generally be that vein which is most superficial thereby giving rise to the greatest local heating effect. The invention also contemplates detection of more than a single "hot spot" along the same vein. In this case, line-fitting between all the detected hot spots affords a determination of the vein's locus.

During use, the instrument is switched on whereupon the On/Off lamp illuminates. The instrument is placed at the correct location on the patient's forearm or wrist or any other place, as required. Scanning is now performed and during which the scan signal is sampled. Either at the completion of the scanning or during scanning, if desired, the scan signal is processed and if a vein is located, its location is marked. If no vein is located, then as noted above, an audible (or other) warning is given. In this case, the instrument is moved to another location and the process is repeated, as required, until a vein is successfully located. Upon successful location of a vein, the instrument is moved and the required medical procedure is carried out.

The infrared detector 12 should be operative within a range of between 3 and 20 $\mu$. The instrument is intended to operate up to a depth of 5 to 7 mm, with a scan resolution in the order of 0.1 mm.

Figure 4:
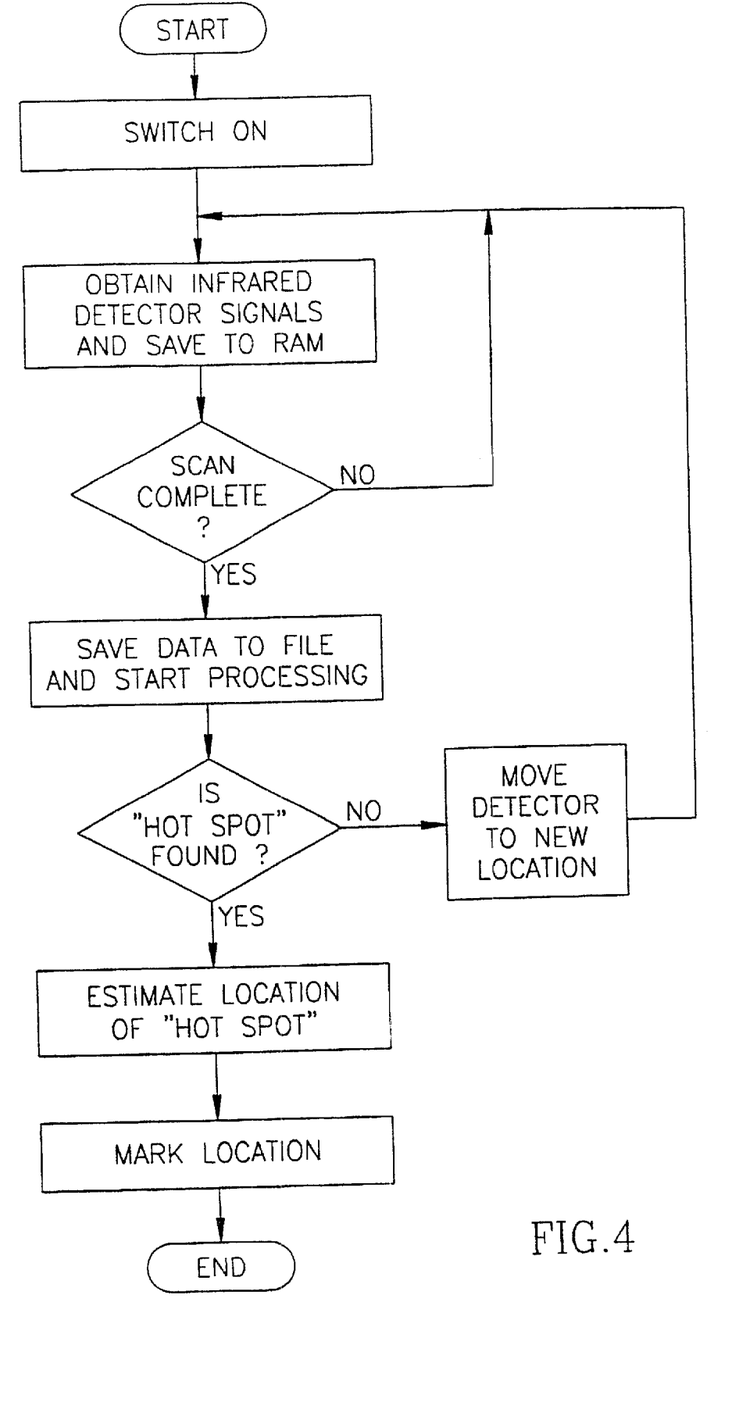
FIG. 4 is a flow diagram showing the principal of operating steps of an instrument, which locates and marks an area of body tissue, based on infrared detection.

Having described with reference to FIGS. 3A and 3B a specific implementation using the optical scanning mechanism of FIGS. 2A and 2B, there will now be described with reference to FIG. 4 a more general approach amenable to other types of detector and scanning. Thus, FIG. 4 is a flow chart showing generally applicable operating steps of an instrument according to the invention, based on infrared detection. On "power on" the IR detector is activated and IR detection commences so as to determine discrete signals representative of respective temperatures of discrete points along an unstimulated portion of body tissue. Data representative of the discrete signals are stored in RAM memory. At the conclusion of this scanning process, the data is saved to a file and data processing commences so as to locate a "hot spot" as described above. Once the area of the body tissue is found, its location is estimated and marked. If no "hot spot" is found, then the detector is moved to a new location and the cycle is repeated.

Figure 5:
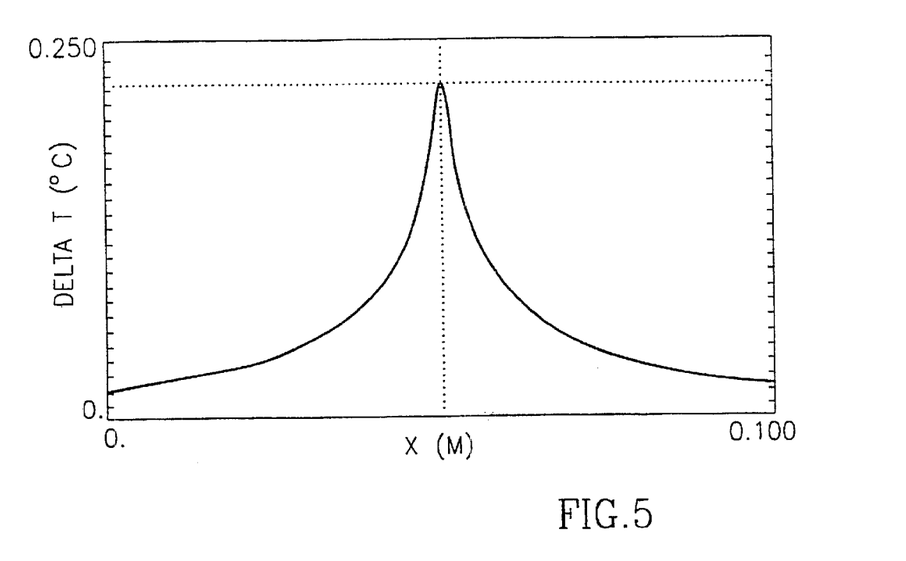
FIGS. 5 to 7 are graphical representations showing temperature profiles and derivatives thereof for explaining in more detail the flow diagram shown in FIG. 3.

FIG. 5 is a temperature profile showing ΔT as a function of distance along the measured limb showing a single peak at a distance of 49.91 mm measured from a nominal origin point. This curve shows that a single vein is located at the measured abscissa thus allowing straightforward, unambiguous detection of the vein.

Figure 6:
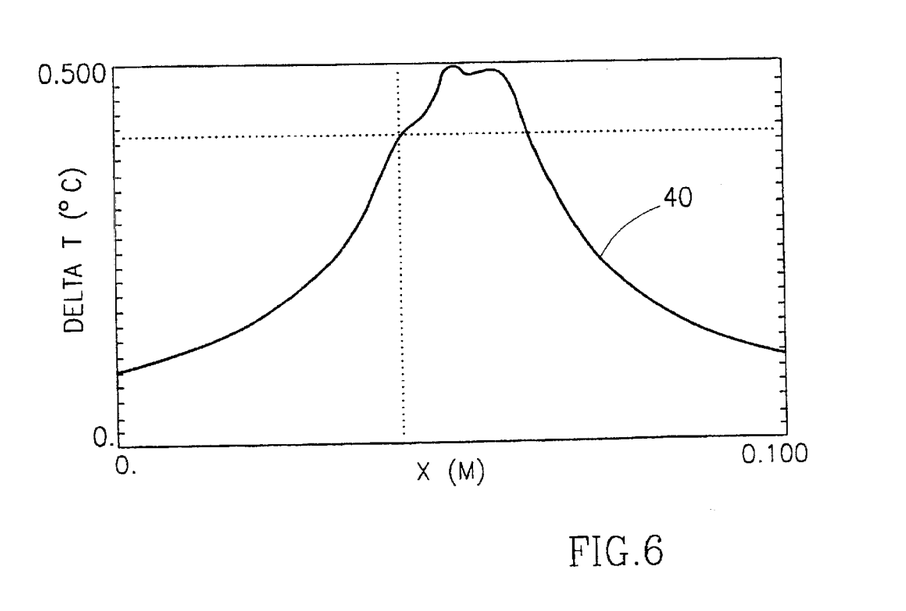

The presence of other veins in the same vicinity may modify the location of temperature peak maxima. Thus, for example, FIG. 6 shows a temperature profile 40 associated with more than one vein wherein the number of veins as well as their respective locations cannot be a priori established.

Figure 7:
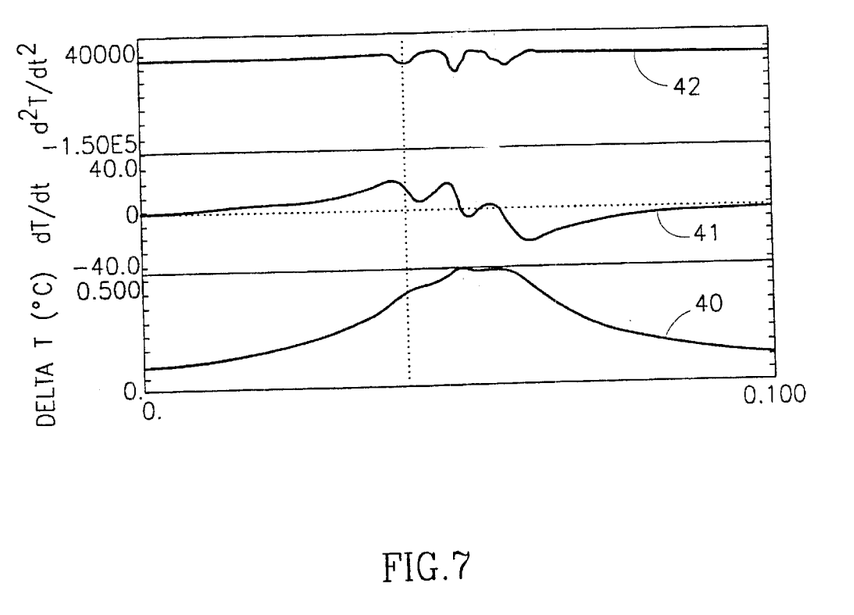

However, as shown in FIG. 7, the first derivative 41 reveals three peaks whilst the second derivative 42 reveals three troughs, thus clearly establishing the presence of at least three separate veins. It is thus clear that the correct determination of the veins' location cannot be determined merely from the temperature profile itself and that to obtain an unambiguous determination, reference must be made to the derivatives of the temperature profile.

Based on the above, the actual steps of implementation are as follows:

(1) Read the observation data file containing observation abscissae and measured temperatures.
(2) Smooth out the temperature profile, so as to obtain the smoothed first and second derivatives.
(3) Process the temperature profile and derivatives so as to detect the respective veins and obtain an initial estimation of the veins' respective abscissae.
(4) Construct a set of initial estimates including all parameters that are not accurately known in advance, for instance tissue thermal conductivity, heat transfer coefficient, etc.
(5) Refine this estimated parameter vector using non-linear iteration.
(6) Post-analyze the final estimated parameter vector so as to filter out bad results and spurious veins.
(7) If post-analysis has invalidated or removed some fictitious veins, repeat from step (4).

The above steps allow ambiguities associated with multiple veins in near proximity to be resolved.

Detection of Vein Abscissae:
  Within the global observation region, the first reference vein is located as corresponding to the peak of the temperature profile. This location is then refined by locating the minimum of the second derivative in its vicinity.
  From this point, an iterative search procedure is used in order to obtain estimated locations of other veins.
  A possible vein location is decided when recognizing a temperature maximum (with change of sign of the first derivative), or a minimum of curvature (second derivative).
  It is essential to note that, in real situations, this procedure would always result in the false detection of spurious veins, in particular because of noise which manifests itself in the derivatives.
  Some criteria are used to reject false veins at this stage (e.g. consideration of only the important minima of curvature).
  Nevertheless, spurious veins are likely to be present at this stage and they will have to be removed later according to a set of rejecting criteria including:
    Veins whose proximity to another vein is less than a predetermined threshold.
    Veins with depth equal to the fixed maximum.
    Veins with heat flow equal to the fixed minimum.

In the preferred embodiment, the temperature scanning means is realized by an infrared detector in combination with a lens and folding optics. However, any other suitable imaging system may equally well be employed, such as mirrors instead of lenses; or by means of proximity detectors using one or more optical elements. Likewise, although the preferred embodiment employs linear scanning, it will be clear that scanning along any desired curve may also be employed, as well as scanning along successive points. The scanning requires that each scan signal be sampled. The sampling is best performed at fixed time intervals.

It should also be noted that in the preferred embodiment the scanning mechanism is adapted to move only the optical components whilst the detector itself remains stationary. However, other scanning mechanisms are also contemplated within the ambit of the invention. Thus, for example, movement of only the detector using stationary optics is also possible. Also, the infrared detector and associated optics may be moved together. Alternatively, scanning may be effected without moving parts by reading an array of stationary detectors. Such a detector can be constituted by a infrared-sensitive chip mounted in contact with the skin, in which case no optics or scanning mechanism are required.

The electronics have not themselves been described in detail because they are all known per se. The function of the electronics is to amplify the detector signal and to filter out unwanted noise. The filtering can be accomplished using discrete components or by means of a custom DSP chip (Digital Signal Processor) or by means of software.

In the preferred embodiment, location of a vein is marked by means of an LED. The light produced thereby may, if desired, be pulsating; and may be white light or composed of several colors. In the case where pulsating light is used, the pulsating may be accomplished electronically or by means of an optical shutter. Preferably, the light is pulsed by means of the chopper, which also serves to modulate the detector signal so as to compensate for changes in phase or frequency. However, the invention also contemplates marking the skin by means of an ink spot or other pigment via an ink jet nozzle or other suitable instrument controlled by the processing unit 25 so as to be brought into alignment with the point of maximum temperature in a substantially analogous manner to that described above.

It will also be appreciated that whilst, in the preferred embodiment, the pulsating LED beam is produced mechanically via the chopper 13, the pulsating beam can also be produced electronically using standard pulse circuits which are well known in the art.

In the preferred embodiment, an infrared detector is employed. However, it will be understood that other suitable thermal radiation detectors can equally well be used.

Likewise, although in the preferred embodiment rechargeable or non-rechargeable batteries are used to power the electronics, this is not mandatory and an external power source may be employed albeit at the cost of rendering the instrument less portable.

As noted above, the chopper serves to modulate the detector signal and can be implemented using an oscillating mirror, an optical shutter employing moving metal leaves or a rotating disc having slots as proposed in the preferred embodiment.

The instrument is packaged in a housing formed by any suitable material, such as plastics. Under certain circumstances it may be desirable to overlay the plastics with a metal coating in order to provide electromagnetic screening. An opening in the housing allows the passage therethrough of thermal energy as well as the visible light beam where an LED or other light source is employed.

The invention has been described with particular regard to the location and marking of at least one vein for the purpose of carrying out a surgical procedure. However, the invention contemplates more general application as will now be described briefly. First, a "hot spot" may result from the increased flow of blood through a vein or artery thus causing local heating of an area of body tissue or, to the contrary, from a blockage in a vein or artery causing an increased quantity of blood to accumulate. This also creates local heating of an area of body tissue and is thus equally amenable to detection and location according to the principles of the invention. The same applies to any other physiological artifact causing a local variation in temperature of body tissue such as, for example, tumors, growths and so on.

What is claimed is:

1. A portable passive instrument for locating and marking at least one area of a person's body tissue having a local variation in temperature compared with surrounding body tissue, said instrument comprising:

a temperature scanning unit for scanning along the person's skin within a region of said body tissue so as to obtain signals representative of a temperature profile along an unstimulated portion of the skin, a processing unit coupled to said temperature scanning unit for analyzing said signals so as to derive the temperature profile in order to determine said at least one area having local temperature variation, and a marking unit for marking said at least one area;

characterized in that:

the temperature scanning unit is adapted for scanning along at least a line of skin within the region of said body tissue so as to obtain discrete signals representative of respective temperatures of discrete points along an unstimulated portion of the at least a line of skin, the processing unit is further adapted to process the temperature profile by determining first and second derivatives of the temperature profile in order to compensate for a possible influence of multiple veins in close mutual proximity so as to determine a location of each vein within the scanned region of body tissue, and the marking unit is adapted to mark at least one vein within the scanned region of body tissue.

2. The instrument according to claim 1, wherein the temperature scanning unit includes an infrared detector array for imaging said discrete points so as to produce said discrete signals.

3. The instrument according to claim 1, wherein the temperature scanning unit includes an infrared detector coupled to a scanning mechanism for advancing the detector to successive imaging points so as to produce said discrete signals successively.

4. The instrument according to claim 3, wherein the temperature scanning unit includes a chopper for modulating the detector signals.

5. The instrument according to claim 3, wherein the scanning mechanism includes an optical scanner for directing thermal radiation from said discrete points towards the infrared detector.

6. The instrument according to claim 3, wherein the scanning mechanism includes a scan mirror and associated folding optics.

7. The instrument according to claim 2, wherein the infrared detector is adapted to detect radiation having a wavelength between 3–20 $\mu$m.

8. The instrument according to claim 1, wherein the processing unit includes:

a memory for storing said discrete signals, means coupled to the memory for determining from the temperature profile at least one peak corresponding to a respective area of body tissue along the at least one scanned line of skin, and a correlator for correlating the at least one peak with a respective discrete point of the skin so as to determine a corresponding location of said discrete point along the skin.

9. The instrument according to claim 1, wherein the marking unit includes a point light source responsively coupled to the processing unit for illuminating said at least one area.

10. The instrument according to claim 3, wherein:
the marking unit includes a point light source responsively coupled to the processing unit for illuminating said at least one area corresponding to a known position of the scanning mechanism, and
the scanning mechanism is adapted to move to said known position and is operatively coupled to the point light source for directing the point light source to illuminate the at least one area.

11. The instrument according to claim 1, wherein the marking unit is responsively coupled to the processing unit for marking the at least one area with a pigment.

12. The instrument according to claim 1, wherein there are derived at least two areas having local heating and the processing unit further includes a locus determination unit responsive to said at least two areas for determining a best-fit line intersecting said at least two areas such that said best-fit line defines the locus of the vein.

13. The instrument according to claim 1, wherein the processing unit is adapted to perform the following steps:
i) process the temperature profile and first and second derivatives so as to detect the respective veins and obtain an initial estimation of the veins' respective abscissae,
ii) construct an estimated parameter vector including a set of initial estimates including parameters that are not accurately known in advance,
iii) refine the estimated parameter vector using non-linear iteration so as to produce a refined estimated parameter vector,
iv) post-analyze the refined estimated parameter vector so as to filter out bad results and spurious veins,
v) if post-analysis has invalidated or removed some fictitious veins, repeat from step ii).

14. A method for locating and marking at least one area of a person's body tissue having a local variation in temperature compared with surrounding body tissue, said method comprising the steps of:
(a) scanning along the person's skin within a region of said body tissue so as to obtain detector signals representative of a temperature profile along an unstimulated portion of the skin, and
(b) analyzing said signals so as to derive the temperature profile in order to determine said at least one area having local temperature variation, and
(c) marking said at least one area, characterized in that:
i) step (a) is performed along at least a line of skin within the region of said body tissue and step (a) further includes obtaining discrete signals representative of respective temperatures of discrete points along an unstimulated portion of the at least a line of skin,
ii) step (b) further includes processing the temperature profile by determining first and second derivatives of the temperature profile in order to compensate for a possible influence of multiple veins in close mutual proximity so as to determine a location of each vein within the scanned region of body tissue, and
iii) step (c) includes marking at least one vein within the scanned region of body tissue.

15. The method according to claim 14, wherein step (a) includes imaging said discrete points on a detector array.

16. The method according to claim 14, wherein step (a) is performed mechanically.

17. The method according to claim 16, further including the step of modulating the detector signals.

18. The method according to claim 14, wherein step (a) is performed optically.

19. The method according to claim 14, wherein step (b) includes:
i) storing said discrete signals,
ii) determining from the temperature profile at least one peak corresponding to a respective area of body tissue along the at least one scanned line of skin, and
iii) correlating the at least one peak with a respective discrete point of the skin so as to determine a corresponding location of said discrete point along the skin.

20. The method according to claim 14, wherein step (c) includes illuminating said at least one area.

21. The method according to claim 14, wherein step (c) includes marking the at least one area with a pigment.

22. The method according to claim 14, wherein there are derived at least two areas along a vein having local heating and there is further included the step of:
(d) determining a best-fit line intersecting said at least two areas such that said best-fit line defines the locus of the vein.

23. The method according to claim 14, wherein step (b) includes:
i) processing the temperature profile and first and second derivatives so as to detect the respective veins and obtain an initial estimation of the vein's respective abscissae,
ii) constructing an estimated parameter vector including a set of initial estimates including parameters that are not accurately known in advance
iii) refining the estimated parameter vector using non-linear iteration so as to produce a refined estimated parameter vector,
iv) post-analyzing the refined estimated parameter vector so as to filter out bad results and spurious veins,
v) if post-analysis has invalidated or removed some fictitious veins, repeat from step ii).

* * * * *